US008530614B1

(12) United States Patent
Wang et al.

(10) Patent No.: US 8,530,614 B1
(45) Date of Patent: Sep. 10, 2013

(54) PORPHYRIN COORDINATION POLYMER NANOSPHERES AND NANORODS

(71) Applicant: Sandia Corporation, Albuquerque, NM (US)

(72) Inventors: Zhongchun Wang, Sunnyvale, CA (US); John A. Shelnutt, Tijeras, NM (US); Craig J. Medforth, Oporto (PT)

(73) Assignee: Sandia Corporation, Albuquerque, NM (US)

( * ) Notice: Subject to any disclaimer, the term of this patent is extended or adjusted under 35 U.S.C. 154(b) by 0 days.

(21) Appl. No.: 13/664,170

(22) Filed: Oct. 30, 2012

Related U.S. Application Data

(62) Division of application No. 11/762,512, filed on Jun. 13, 2007, now Pat. No. 8,324,342.

(51) Int. Cl.
  *C08G 79/00* (2006.01)
  *C07B 47/00* (2006.01)
  *C07D 487/22* (2006.01)
(52) U.S. Cl.
  USPC .......................................... 528/395; 540/145

(58) Field of Classification Search
  USPC .......................................... 528/395; 540/145
  See application file for complete search history.

(56) References Cited

PUBLICATIONS

Goldberg Denmark and Siegel, Topics in Sterochemistry, vol. 25, Chapter 3, 2006.*
Wang et al. J. Am. Chem. Soc. 2004, 126, 16720-16721.*
Fujita et al. Angew. Chem. Int. Ed. 2001, 40(9), 1718-1721.*

* cited by examiner

*Primary Examiner* — Liam Heincer
(74) *Attorney, Agent, or Firm* — Carol I. Ashby; Kevin W. Bieg

(57) ABSTRACT

A porphyrin coordination polymer nanostructure comprising a network of pyridyl porphyrin molecules and coordinating metal ions coordinatively bound through the pyridyl groups. In some embodiments, the porphyrins are metalloporphyrins. A variety of nanostructures are formed by the network polymer, including nanospheres, polygonal nanostructures, nanorods, and nanofibers, depending on a variety of factors including coordination metal ion, porphyrin type, metal of the metalloporphyrin, and degree of agitation during nanostructure formation. Reduction of coordinating metal ions may be used to form metal nanoparticles on the coordination polymer nanostructure.

11 Claims, 11 Drawing Sheets

Pt-SnT(4Py)P rods made with stirring

SEM

Pt-SnT(4Py)P made without agitation

TEM of Pt-SnT(4Py)P

Pt-SnT(3Py)P made without agitation

Pt-FeT(4Py)P TEM

Pt-CoT(4Py)P TEM

Pt-SnT(4Py)P rods made with stirring

SEM

Pt-TiOT(4Py)P

Pt-VOT(4Py)P

Pd(IV)-SnT(4Py)P

Ru(IV)-SnT(4Py)P

Cu-H₂TPyP

Pt-H$_2$T(4Py)P

Pt-H$_2$DPyDPP

Pt-SnT(4Py)P nanospheres
with Pt nanodendrites

Pt-SnT(4Py)P nanosphere
with Pt nanodendrites

PORPHYRIN COORDINATION POLYMER NANOSPHERES AND NANORODS

This application is a divisional application of the prior-filed copending U.S. nonprovisional patent application Ser. No. 11/762,512, filed on Jun. 13, 2007, and claims priority benefit therefrom. This prior-filed copending application is hereby incorporated by reference.

The United States Government has rights in this invention pursuant to Department of Energy Contract No. DE-AC04-94AL85000 with Sandia Corporation.

BACKGROUND OF THE INVENTION

This invention relates to heteroporphyrin nanostructures comprising metalloporphyrin coordination polymers.

Abrahams and coworkers reported the formation of 3D polymeric network of Pd-tetra(4-pyridyl)porphyrin (Pd-T(4-Py)P) connected through trans-coordination of pyridyl nitrogens to $Cd(NO_3)_2(H_2O)_2$ moieties that were formed in boiling 1:1 methanol:water+boiling ethanol. Crystals suitable for X-ray diffraction analysis precipitated upon cooling. (B. F. Abrahams, B. F. Hoskins, and R. Robson, "A New Type of Infinite 3D Polymeric Network Containing 4-centered, Peripherally Linked Metalloporphyrin Building Blocks," J. Amer. Chem. Soc. (1991) vol. 113, pp. 3606-3607.)

Pan et al. reported formation of $Hg(H_2TPyP)$ microcrystalline solid by combination of a methanol solution of $HgBr_2$ and a chloroform solution of $H_2TPyP$. Slow precipitation produces plate-like crystals suitable for X-ray analysis. (L. Pan, B. C. Noll, and X. Wang, "Self-Assembly of free-base tetrapyridylporphyrin units by metal ion coordination," Chem. Commun. (1999) pp. 157-158.)

Sharma and coworkers have reported coordination complexes of metal halides ($MX_2$ (M=Cd, Hg, Pb; X=Br, I) with freebase tetrapyridylporphyrin (TPyP) that form either 1-D $[(HgX_2)_2TPyP]\cdot 2TCE$ or 2-D $[(MX_2)TPyP]\cdot 4$ TCE (M=Pb, Cd) where TCE is 1,1,2,2-tetrachloroethane. The TPyP was metalated with $Zn^{2+}$, $Cu^{2+}$, and $Ni^{2+}$. The single crystals of TPyP coordination polymers (freebase, partially and fully metallated) were grown using a layering technique at ambient temperatures in which TPyP was dissolved in 3:1 solution mixtures of TCE and methanol and then layered with metal salts dissolved in methanol. (C. V. K. Sharma, G. A. Broker, J. G. Huddleston, J. W. Baldwin, R. M. Metzger, and R. D. Rogers, "Design Strategies for Solid-State Supramolecular Arrays Containing Both Mixed-Metalated and Freebase Porphyrins," J. Amer. Chem. Soc. (1999) vol. 121, pp. 1137-1144.)

Krupitsky and coworkers have described the formation of oligomers involving pyridine meso-substituted porphyrins axially coordinated to the metal ion center of adjacent metalloporphyrin molecules. Coordination polymers form through ligation of the porphyrin periphery on one molecule to the metal center of an adjacent porphyrin. (H. Krupitsky, Z. Stein, I. Goldberg, and C. H. Strouse, "Crystalline Complexes, Coordination Polymers, and Aggregation Modes of Tetra(4-pyridyl)porphyrin," J. Inclusion Phenomena and Molecular Recognition in chemistry (1994) vol. 18, pp. 177-192.)

Drain and coworkers report the formation of nanoscale colloidal particles of hydrophobic porphyrins such as 5,10,15,20-tetraphenylporphyrin (TPP), 2,3,7,8,12,13,17,18-octaethylporphyrin (OEP) and the metallo derivatives by adding water (guest solvent) to a solution of the hydrophobic porphyrin in THF, DMSO, DMF, or $CH_3CN$ (host solvent) with a few percent of a low molecular weight PEG such as $HO(C_2H_4O)_4CH_3$ or a non-ionic surfactant. Stabilizers such as PEG are essential for the formation of stable colloidal systems by host-guest solvent methods. The rate an efficiency of mixing the host and guest solvents have a profound effect on the size and stability of the porphyrinic nanoparticles-especially when metalloporphyrins are used. In general for a given derivative and using the same rate of addition, the greater the mixing the small the nanoparticles. The size of the colloidal particles of free base TPP decreases in the order: no stirring, a magnetic stir-bar with a vortex, a vortex mixer, and sonication. 'Stable metalloporphyrin particles are generally formed only when sonication is used. (C. M. Drain, G. Smeureanu, S. Patel, X. Gong, J. Garno, and J. Arijeloye, "Porphyrin nanoparticles as supramolecular systems," New Journal of Chemistry (2006) vol. 30, pp. 1834-1843).

Diskin-Posner and co-workers have reported that metalated 5,10,15,20-tetraphenylporphyrins can be axially linked to each other with the aid of amine and diamine ligands. Seven crystalline materials consisting of such heterogeneous coordination oligomers and polymers of Zn(II)— or Mn(II)-tetraphenylporphyrins have been prepared and characterized by X-ray crystallography. Ligands of varying length have been used as bridging auxiliaries between the metal centers of the porphyrin species. A homogenous coordination polymer of Zn(II)-tetrapyridylporphyrin derivative was also reported. The polymeric arrays in this compound are composed of two crystallographically independent porphyrin units oriented perpendicularly to one another, one with a five-coordinated and the other with a six-coordinated zinc ion. They are arranged in an alternating manner along the polymer. Every building block has three connections to the neighboring molecules. The six-coordinated porphyrin links axially to two five-coordinated species located on opposite sides of its planar core ring, and laterally through one of its pyridyl rings to another five-coordinate moiety. Simultaneously, every five-coordinate molecule associates with three six-coordinate porphyrins through two of its trans-related pyridyl rings as well as by attracting the pyridyl group of another unit to its central zinc ion. (Y. Diskin-Posner, G. K. Patra, and I. Goldberg, "Supramolecular assembly of metalloporphyrins in crystals by axial coordination through amine ligands," J. Chem. Soc., Dalton Trans., (2001) pp. 2775-2782.)

Yuan and coworkers have reported the synthesis of multi-porphyrin and porphyrin-viologen assemblies linked in square planar arrays by Pd(II) or Pt(II) ions. The porphyrins used in their work are monopyridyltriarylporphyrins and the corresponding Zn-substituted monopyridyltriaryl porphyrin. Pyridyl porphyrin metal complexes with a $d^8$ metal ion coordinated to the pyridyl nitrogen can be readily synthesized by treating the appropriate porphyrin with $M(DMSO)_2Cl_2$ (M=Pt, Pd) in refluxing $CHCl_3$. The complexes remain intact in solution for weeks and in the solid state for more than one year. Replacement of the second DMSO ligand requires slightly higher reaction temperatures; treating with a second equivalent of $(PyPP))H_2$ in refluxing toluene results in the clean formation of cis-Pt[(PyPP)$H_2]_2Cl_2$ from cis-Pt(DMSO)[(PyPP)$H_2]Cl_2$. (H. Yuan, L. Thomas, and L. K. Woo, "Synthesis and Characterization of Mono-, Bis-, and Tetrakis-pyridyltriarylporphyrin Pd(II) and Pt(II) Supramolecular Assemblies. Molecular Structure of a Pd-Linked Bisporphyrin Complex," Inorg. Chem. (1996) vol. 35, pp. 2808-2817.)

Drain and coworkers have reported a discrete supramolecular array of nine porphyrins (freebase or metallated with $Zn^{2+}$ ions) by titration of $PdCl_2(NCPh)_2$ into a solution of monopyridyl triphenyl porphyrin, dipyridyl diphenyl porphyrin, and tetrapyridyl porphyrin (4:4:1) in toluene, mineral oil, or chloroform. (C. M. Drain, F. Nifiatis, A. Vasenko, and J. D. Batteas, "Porphyrin Tessellation by Design: Metal-Mediated Self-Assembly of Large Arrays and Tapes," Angew. Chem. Int. Ed. (1998) vol. 37, pp. 2344-2347.)

Carlucci and co-workers report the formation of [Ag$_4$(H$_2$tpyp)$_3$](NO$_3$)$_4$.x solvent, [Ag$_2$(H$_2$tpyp)$_3$(NO$_3$)](NO$_3$).x solvent, and [Ag$_8$(Zntpyp)$_7$(H$_2$O)$_2$](NO$_3$)$_8$.x solvent by diffusing AgNO$_3$ dissolved in N,N'-dimethylacetamide (DMA) into a tetrachloroethane/methanol (TCE/MeOH) solution of the free base or Zn$^{2+}$-substituted tetra pyridyl porphyrin (TPyP). (L. Carlucci, G. Ciani, D. M. Proserpio, and F. Porta, "Open Network Architectures from the Self-Assembly of AgNO$_3$ and 5,10,15,20-Tetra(4-pyridyl)porphyrin (H$_2$tpyp) Building Blocks: The Exceptional Self-Penetrating Topology of the 3D Network of [Ag$_8$(Zn$^{II}$tpyp)$_7$(H$_2$O)$_2$](NO$_3$)$_8$," Angew. Chem. Int. Ed. (2003, vol. 43, pp. 317-322.)

Shelnutt et al. ("Dendritic Metal Nanostructures," filed Jul. 8, 2004, "U.S. patent application Ser. No. 10/887,535) describes the deposition of metal dendrites on the surface of a surfactant structure template, such as a micelle, a liposome, a vesicle, or a membrane.

Shelnutt et al. describes the formation of porphyrin nanotubes that are not coordination polymers ("Heteroporphyrin Nanotubes and Composites," U.S. Pat. No. 7,132,163 and "Heteroporphyrin Nanotubes and Composites," U.S. Pat. No. 7,223,474).

BRIEF DESCRIPTION OF THE DRAWINGS

The accompanying drawings, which are incorporated in and form part of the specification, illustrate an embodiment of the present invention and, together with the description, serve to explain the principles of the invention.

DETAILED DESCRIPTION OF THE INVENTION

Figure 1:
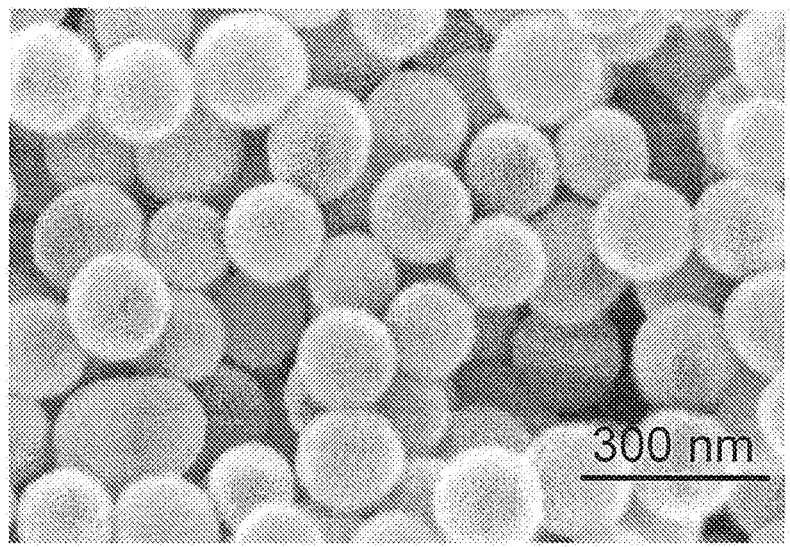
FIG. 1 is a scanning electron micrograph (SEM) of Pt—SnT4PyP nanospheres formed with minimization of agitation during the nanostructure formation step.

This invention comprises porphyrin nanostructures formed from coordination polymers comprising pyridyl-substituted porphyrins and coordinating metal ions linking the pyridyl-substituted porphyrins by binding to the nitrogen atoms of the pyridyl groups. A pyridylporphyrin is defined herein as a porphyrin comprising at least two substituent pyridyl groups positioned such as to be sterically available for binding as a ligand to a connecting metal ion to form a network that is the porphyrin coordination polymer. Examples include tetra(4-pyridyl)porphyrin (T(4Py)P), tetra(3-pyridyl)porphyrin (T(3Py)P) and dipyridyldiphenylporphyrin (DPyDPP). The nanostructures comprise freebase and/or metallated 5,10,15,20-tetrapyridylporphyrin (TPyP), which is either T(3Py)P or T(4Py)P, and/or freebase and/or metallated dipyridyldiphenyl porphyrin. The 5,10,15,20 substituent site configuration is also termed a meso configuration. Unless otherwise stated, a meso configuration is assumed in the following discussions. A plurality of nitrogen atoms of the pyridyl rings bind to coordinating metal ions to form an extended network. The invention further comprises methods for forming these structures. A metallopyridylporphyrin is a pyridylporphyrin with a metal ion or metal-oxygen species bound within the porphyrin ring.

Functional self-assembled materials with well-defined shapes and dimensions are of great current interest, especially for applications in electronics, photonics, light-energy conversion, and catalysis. In biological systems, tetrapyrroles such as porphyrins and chlorophylls are often organized into nanoscale biological superstructures that perform light-harvesting and energy- and electron-transfer functions. Because of their desirable functional properties, porphyrins and other tetrapyrroles are attractive building blocks for functional nanostructures.

In some embodiments, this invention comprises heteroporphyrin nanostructures formed from coordination polymers comprising metallated 5,10,15,20-tetrapyridylporphyrin and metal ions that bind to the nitrogen atoms of the pyridyl rings. Both tetra(4-pyridyl)porphyrin and tetra(3-pyridyl)porphyrin have been successfully employed in embodiments of this invention. The abbreviation TPyP refers to both chemical species. The abbreviations T(4Py)P and T(3Py)P are used when appropriate to distinguish between the materials. Dipyridyldiphenyl porphyrin has been employed in some embodiments and is abbreviated DPyDPP.

In some embodiments, MTPyP (a metallated tetrapyridylporphyrin) is dissolved in water to form an aqueous solution of MTPyP. In other embodiments, MTPyP is dissolved using dilute acid or into an aqueous solution containing a salt such as, for example, KCl. In some embodiments, the MTPyP solution may be allowed to stand in air to adjust the oxidation state of the metal. For example, a CoTPyP solution may be allowed to stand in air to provide for the oxidation of residual Co(II) species. In some embodiments, the porphyrin solutions can be stock solutions that are prepared some time in advance of the nanostructure preparation reaction. Porphryin solutions, including stock solutions, may optionally be filtered through a 0.2-micrometer syringe filter to remove any particles and are typically stored in the dark until use, but dark storage is not essential. Storage in light is also possible if the time is sufficiently short or if the conditions are such that undesired photoreactions do not occur to an appreciable extent. The metalloporphyrin solution is combined with a solution of a connecting-ion source, is shaken to substantially homogenize the combined solution, and may be kept in the dark without agitation. Reaction in the light is also possible and agitation may be used; a different nanostructure may result with agitation than without agitation. When agitation is minimized, a very large majority of nanospheres forms in preference to other nanostructures in many embodiments. The yields of well-formed nanospheres are more than 90% for Pt-MTPyP, M=Fe, Co, Sn, TiO, and VO, and Cu—CuTPyP. In this system of nomenclature, for example, Pt is the connection metal ion and M is the metal coordinated within the porphyrin ring. With agitation, other nanostructures are often preferentially formed in many embodiments. Reaction can proceed at room temperature or at another temperature if so desired. In some embodiments, changing the temperature can serve to change the size of the nanostructures that are formed.

Figure 2:
FIG. 2 is a transmission electron micrograph (TEM) of Pt—SnTPyP nanospheres, showing the very smooth surface of the nanospheres.

In one embodiment for the preparation of Pt—SnT(4Py)P nanospheres, 291 microliters of $H_2PtCl_6$ (27.5 mM) (a connecting ion source solution) were injected into 20 mL of SnT(4Py)P solution (100 micromolar concentration). Agitation of the resulting reaction solution was minimized while the nanospheres formed. The resulting nanosphere average diameter was approximately 161±13 nm. FIG. 1 illustrates a scanning electron micrograph (SEM) of Pt—SnT(4Py)P. FIG. 2 illustrates a transmission electron micrograph (TEM) of Pt—SnT(4Py)P showing the smoothness of the surface of nanospheres like those in the SEM of FIG. 1.

Figure 3A:
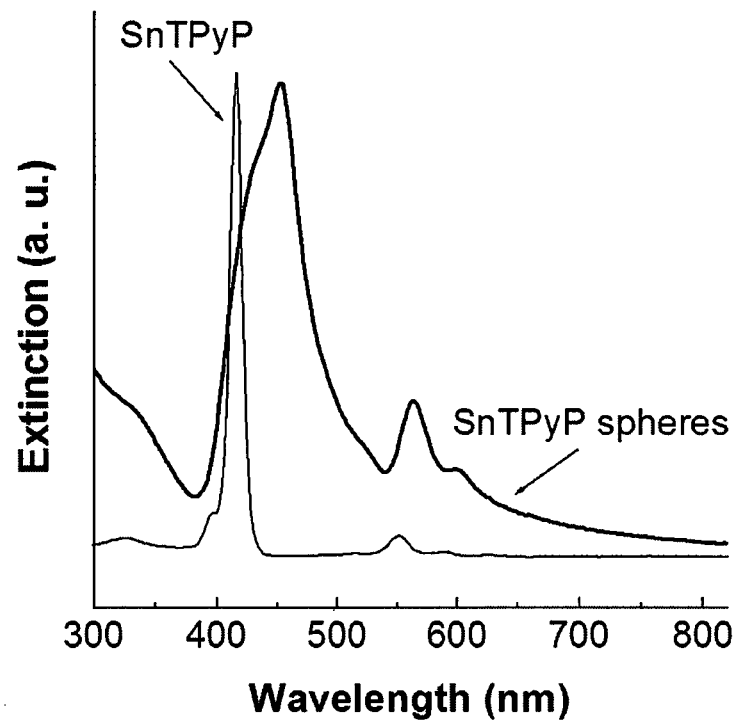
FIG. 3 illustrates the absorption (3a) and emission (3b) spectra of SnT4PyP in solution and of nanospheres of Pt—SnT4PyP coordination polymer.
Figure 3B:
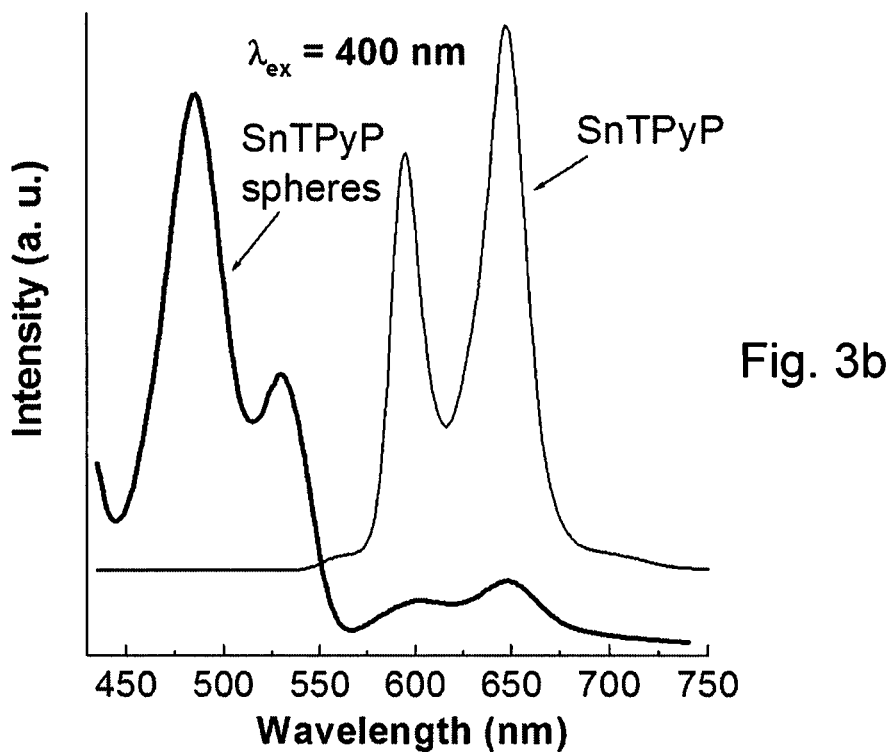

FIG. 3 shows the absorption (FIG. 3*a*) and emission (FIG. 3*b*) spectra of a solution of SnT(4Py)P and of Pt—SnT(4Py)P nanospheres. As compared to the monomeric SnT(4Py)P, the Pt—SnT(4Py)P coordination polymer nanospheres exhibit a broadened and red-shifted absorption profile in the UV-visible region. The Soret band is shifted from 416 nm to 452 nm, while the Q bands shift from 552 and 592 nm to 564 and 602 nm, respectively. The Pt—SnT(4Py)P spheres are fluorescent.

In another embodiments, 200 microliters of 1 N KCl, 100 microliters of 1 N HCl, or 200 microliters of 1 N HCl were added to the SnT(4Py)P solution before injection of the $H_2PtCl_6$ solution. The resulting nanosphere average diameters were approximately 222±40 nm, 229±43 nm, and 273±55 nm, respectively.

Figure 4:
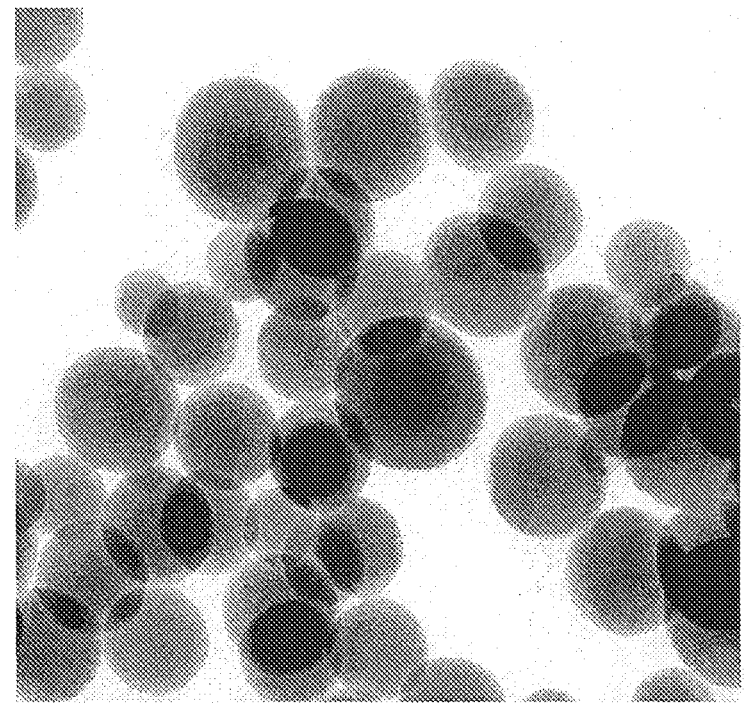
FIG. 4 is a TEM of Pt—SnT3PyP nanospheres formed with minimization of agitation during the nanostructure formation step.

In one embodiment for the preparation of Pt—SnT(3Py)P nanospheres, 291 microliters of $H_2PtCl_6$ (27.5 mM) (a connecting ion source solution) were injected into 20 mL of SnT3PyP solution (100 micromolar concentration). Agitation of the resulting reaction solution was minimized while the nanospheres formed. The resulting nanosphere average diameter was approximately 131±24 nm. FIG. 4 is a TEM illustrating an embodiment where meso-tetra(3-pyridyl)porphyrin was used instead of meso-tetra(4-pyridyl)porphyrin to form Pt—SnT(3Py)P nanospheres.

Figure 5:
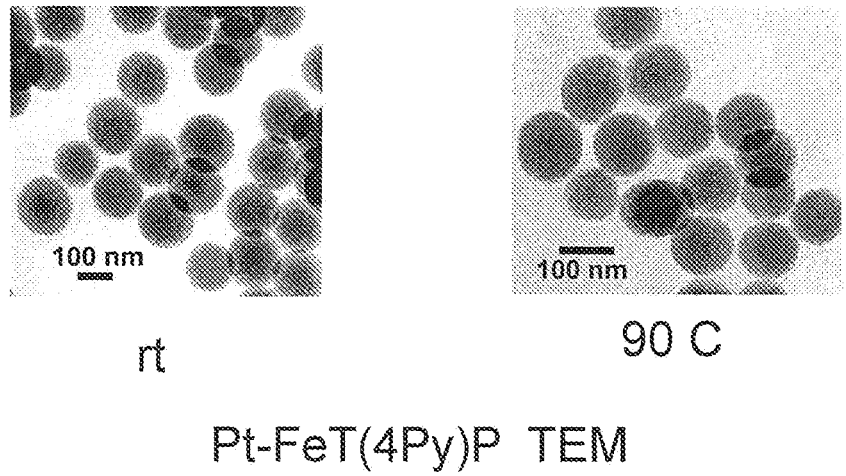
FIG. 5 is a TEM of Pt—FeT4PyP nanospheres formed with minimization of agitation during the nanostructure formation step at either room temperature or at a temperature of 90° C.

In one embodiment for the preparation of Pt—FeT4PyP nanospheres, 596 microliters of 3.358 mM FeT(4Py)P solution in 0.074 M HCl was diluted with water up to 18.4 mL, and then combined with 1.6 mL of 10 mM $H_2PtCl_6$. The resulting nanosphere average diameter was approximately 153±10 nm when prepared at room temperature and 110±6 nm when prepared at 90° C. FIG. 5 presents TEMs of nanospheres made at the two temperatures.

Figure 6:
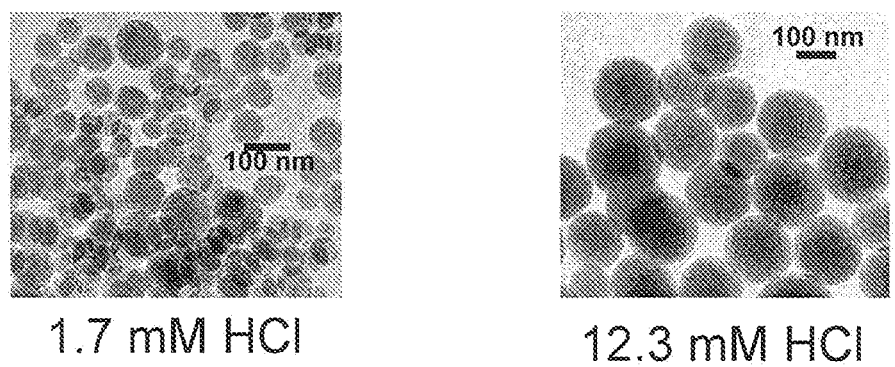
FIG. 6 is a TEM of Pt—CoT4PyP nanospheres formed with minimization of agitation during the nanostructure formation step in solution in an aqueous reaction solution that contained either 1.7 mM HCl or 12.3 mM HCl.

In one embodiment for the preparation of Pt—CoT(4Py)P nanospheres, 343 microliters of 2.913 mM CoT(4Py)P solution in 0.074 M HCl was mixed with zero or 106 microliters of 1 N HCl and diluted with water up to 10 mL before injecting with 145 microliters of 27.5 mM $H_2PtCl_6$. FIG. 6 presents TEMs of nanospheres made at two different solution pH values.

In one embodiment, hybrid nanospheres comprising CoT(4Py)P and SnT(4Py)P were made. In this embodiment, 309 microliters of CoT(4Py)P solution (2913 microM in 0.05M HCl) was combined with 1.0 mL of SnT4PyP (100 microM) and 82 microliters of 1 N HCl. This was diluted with water up to a volume of 10 mL before injecting with 145 microliters of 27.5 mM $H_2PtCl_6$.

Figure 7:
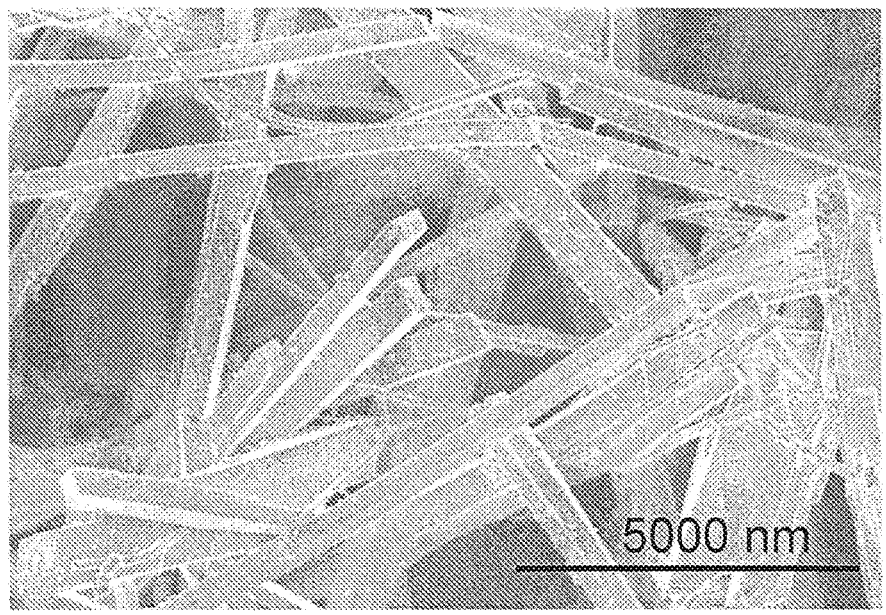
FIG. 7 is a SEM of Pt—SnT4PyP nanorods formed with stirring during the nanostructure formation step.

In some embodiments, for the synthesis of the nanospheres, aqueous solutions of the starting materials are combined, mixed briefly to homogenize, and then stored in the dark undisturbed for a certain length of time (from a few hours to several days). The suitable reaction time depends, among other things, on the type of metalloporphyrin and the reaction temperature. Brown-reddish powder-like precipitates settle out of the solution. Agitation can encourage the formation of rods, as illustrated in FIG. 7 where Pt—SnT(4Py)P nanorods were formed by stirring the solution during nanostructure growth. A small number of nanospheres may form from reaction with agitation.

After the synthesis is complete, the nanospheres are quite stable. For example, Pt—SnT(4Py)P spheres are resistant to change in size and shape after immersion in 0.01M NaOH for 14 hours. They are stable in boiling water. Spheres formed with M-FeTPyP, M-CoTPyP, and Pd-MTPyP exhibit similar stability.

Some embodiments of this invention are quite sensitive to synthesis conditions, including solution conditions such as starting material concentrations and ratios, the solution pH and ionic strength, and the degree of agitation. This sensitivity can be employed to direct the size of nanosphere that is desired from a particular synthesis. Monodisperse nanospheres result from suitable selection of reaction conditions. For the materials shown in FIG. 1, the average diameter, as determined by TEM, was 161.1±12.8 nm. The surfaces appear smooth. Energy dispersive X-ray spectroscopy (EDX) showed the atomic ratios of Sn/Pt and Cl/Pt to be 0.42 and 1.85, respectively. Under the preferred conditions for sphere formation, very uniform spheres are obtained. Under nonpreferred conditions for sphere formation, spheres with a broad size distribution or mixtures of spheres and nanorods may be obtained. For the synthesis of the metalloporphyrin coordination polymer nanospheres, aqueous solutions of the starting materials are mixed, shaken to homogenize, and then stored undisturbed for a period of time, typically between several hours and two weeks. Storage may be with or without illumination. This time range is convenient to use and embodiments of the invention are not restricted to this time range. Other periods of time may be used for the synthesis provided the practitioner of this invention waits for sufficient time for the nanospheres to form. A reddish-brown powder-like precipitate settles out of the solution. Extensive stirring during the polymerization process may encourage the formation of nanorods. Under some agitation conditions, the product is a mixture of nanorods and nanospheres rather than monodisperse nanospheres. A product that is predominantly nanorods can also be produced, as illustrated in FIG. 7.

Figure 8:
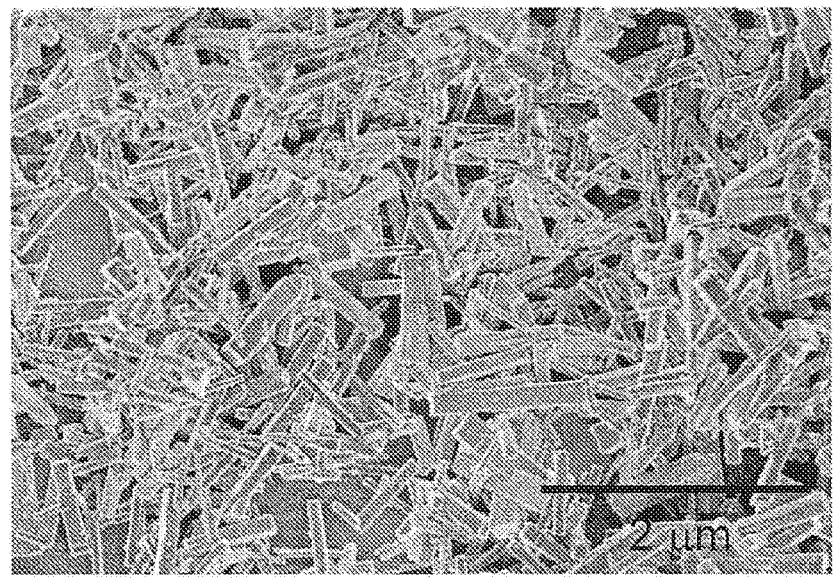
FIG. 8 is a SEM of Pt—TiOT(4Py)P nanorods

In one embodiment for the preparation of Pt—TiOT(4Py)P nanorods, 576 µL of 3.125 mM TiOT4PyP solution in 0.05 M HCl was diluted with water up to 18 mL, and then combined with 720 µL of 10 mM $H_2PtCl_6$. Agitation of the resulting reaction solution was minimized while the nanorods formed. FIG. 8 presents an SEM of the nanorods of this material.

Figure 9:
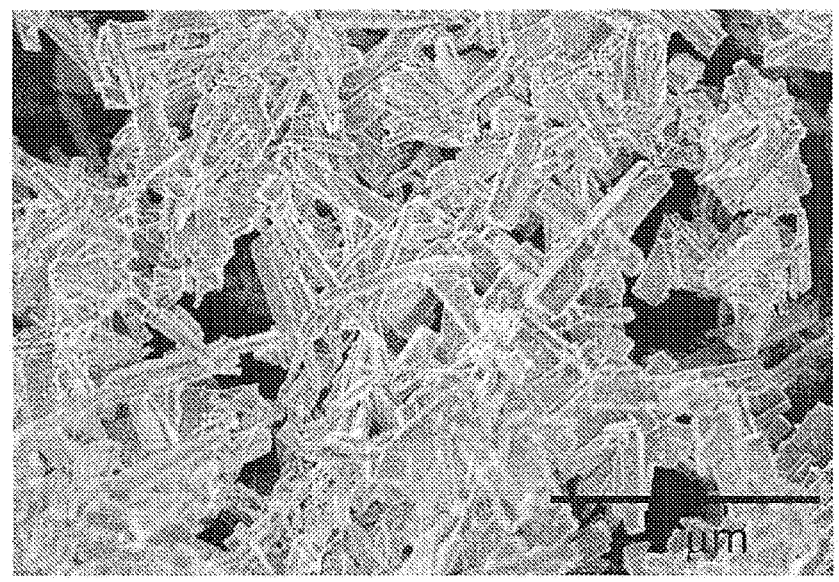
FIG. 9 is a SEM of Pt—VOT(4Py)P nanorods.

In one embodiment for the preparation of Pt—VOT(4Py)P nanorods, 3984 of 4.527 mM VOT4PyP solution in 0.05 M HCl was diluted with water up to 18 mL, and then combined with 1440 μL of 10 mM $H_2PtCl_6$. Agitation of the resulting reaction solution was minimized while the nanorods formed. FIG. 9 presents an SEM of the nanorods of this material.

The nanospheres are stable in organic solvents such as ethanol and dimethylsulfoxide, in water over an extended pH range, and in the dried state. Immersion of the Sn-containing spheres in 0.01M NaOH for 14 hours results in negligible change in the spherical morphology (average diameter change from 161±13 to 159±13 nm) and in the Sn/Pt ratio (change from 0.42 to 0.44). However, the Cl/Pt ratio was reduced from approximately 1.85 to 0.32, presumably due to hydrolysis of residual Pt—Cl bonds present in the nanospheres.

Figure 10:
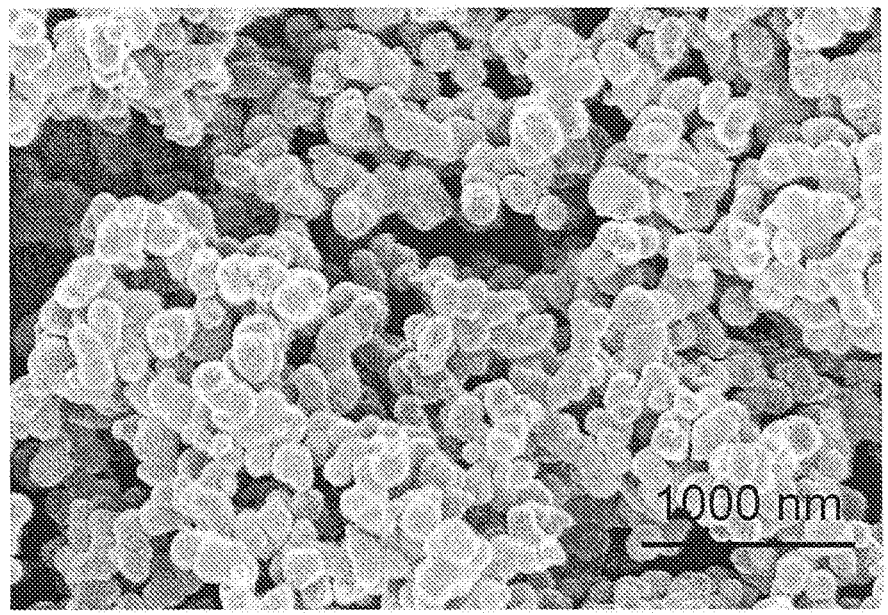
FIG. 10 is a SEM of Ru(IV)—SnT4PyP nanospheroidal clusters formed with minimization of agitation during the nanostructure formation step.

In one embodiment, 0.2 mL of a 20 mM aqueous solution of $(NH_4)_2RuCl_6$ is added to 10 mL of a 100 microM aqueous solution of SnT(4-Py)P. The mixture is shaken for approximately 10 seconds to mix thoroughly (homogenize) and then left in the dark undisturbed (not agitated) until the product precipitates. Nanospheroidal clusters of this material are illustrated in the SEM presented in FIG. 10.

Figure 11:
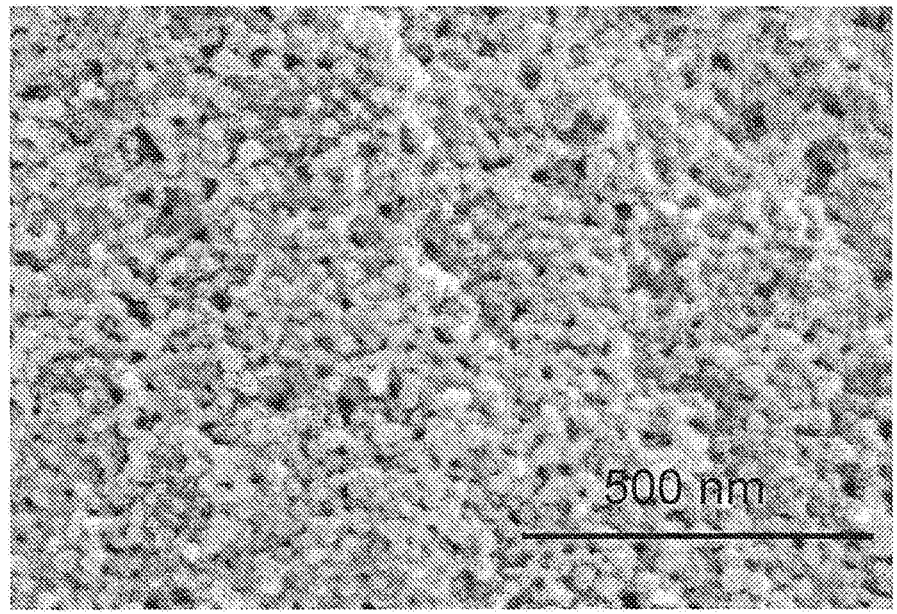
FIG. 11 is a SEM of Pd(IV)—SnT4PyP nanospheroidal cluster formed with minimization of agitation during the nanostructure formation step.

In one embodiment, 0.2 mL of a 20 mM aqueous solution of $(NH_4)_2PdCl_6$ is added to 10 mL of a 100 microM aqueous solution of SnT(4-Py)P. The mixture is shaken for approximately 10 seconds to mix thoroughly (homogenize) and then left in the dark undisturbed (not agitated) until the product precipitates. Nanospheroidal clusters of this material are illustrated in the SEM presented in FIG. 11.

Figure 12:
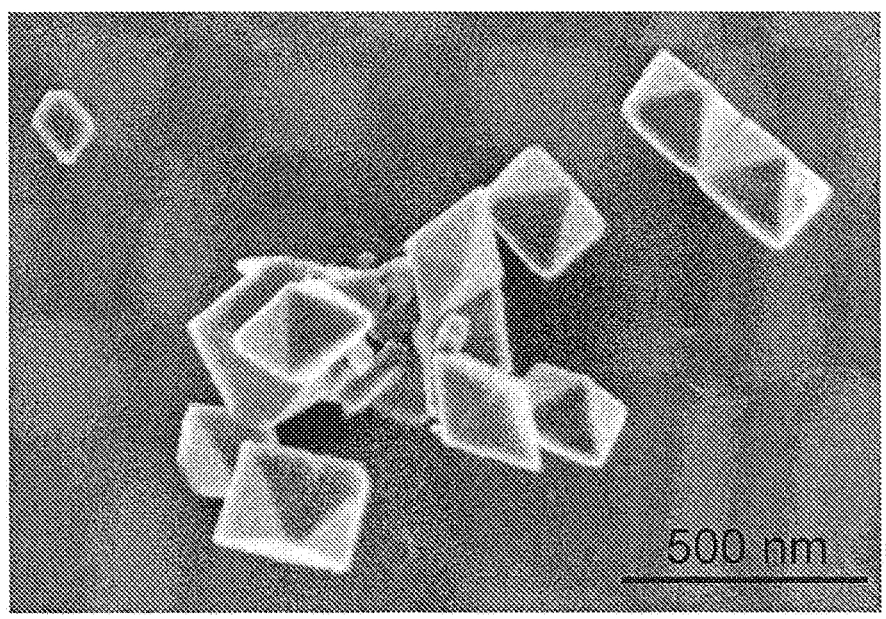
FIG. 12 is an SEM of Cu—H$_2$T4PyP polygonal nanostructure formed with minimization of agitation during the nanostructure formation step.

In one embodiment, 334 microL of 2997 microM $H_2T(4-Py)P$ in 0.136 M HCl was added to 10 mL of water, and the mixture was shaken for approximately 10 seconds to mix thoroughly (homogenize). The mixture was added with 100 microL of 0.2 M Cu(II) acetate, and shaken for approximately 10 seconds to mix thoroughly (homogenize) and then left undisturbed (not agitated) while the nanocrystals form. The polygonal nanocrystals illustrated in FIG. 12 are formed in about one hour.

In one embodiment, 167 microL of 2997 microM $H_2T(4-Py)P$ in 0.136 M HCl was added to 10 mL of water, and the mixture was shaken for approximately 10 seconds to mix thoroughly (homogenize). The mixture was added with 50 microL of 0.2 M Cu(II) acetate, and shaken for approximately 10 seconds to mix thoroughly (homogenize) and then left undisturbed (not agitated). Under these conditions, nanospheres form.

Figure 13:
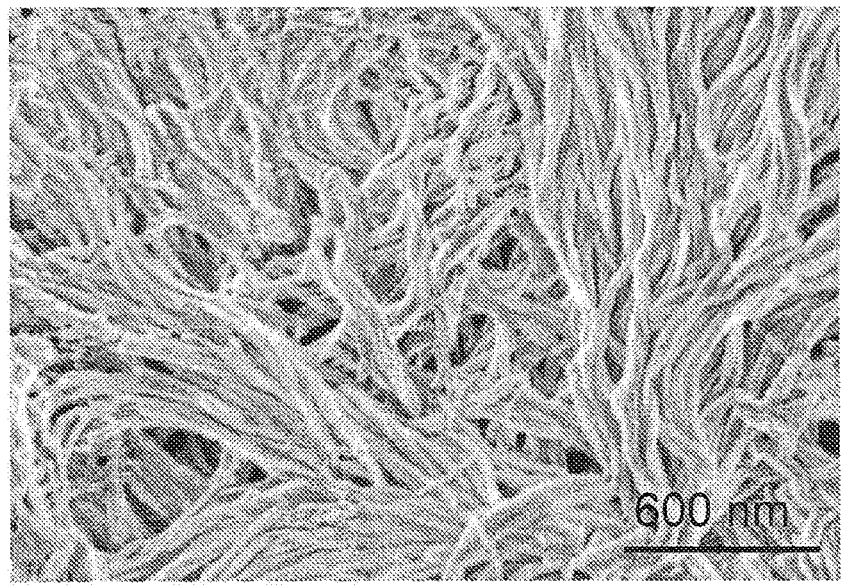
FIG. 13 is a SEM of Pt—H$_2$T4PyP nanofibers.
Figure 14:
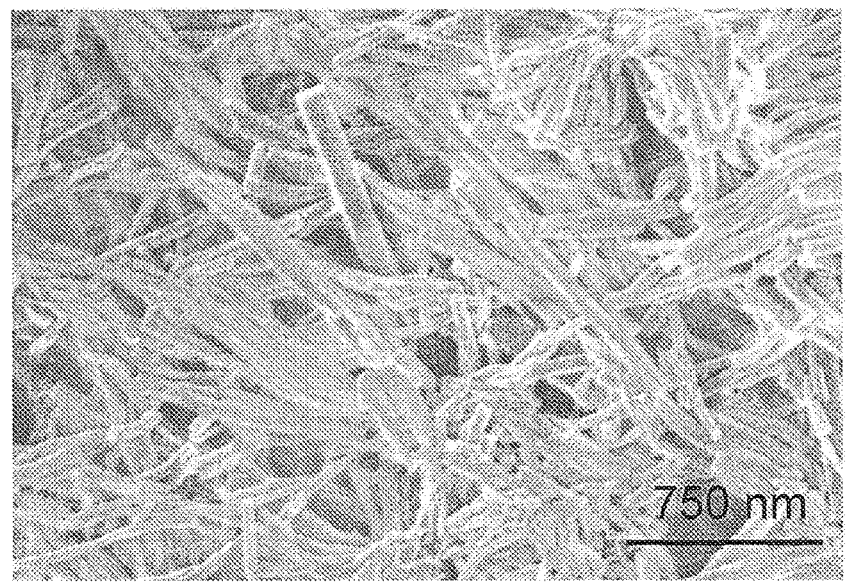
FIG. 14 is a SEM of Pt—H$_2$DPyDPP nanofibers.

In some embodiments employing the freebase porphyrin, nanofibers are formed. In one embodiment, 0.2 mL of a 20 mM aqueous solution of $H_2PtCl_6$ is added to 10 mL of an aqueous solution of 100 microM $H_2T(4-Py)P$ in 0.2 M HCl. The mixture is shaken for approximately 10 seconds to mix thoroughly (homogenize) and then left in the dark undisturbed (not agitated) until the product precipitates as nanofibers (FIG. 13). In another embodiment, 0.2 mL of a 20 mM aqueous solution of $H_2PtCl_6$ is added to 10 mL of an aqueous solution of 100 microM diphenyldipyridylporphyrin (5,15-bis-(4-pyridyl)-10,20-bisphenylporphyrin) in 1 M HCl. The mixture is shaken for approximately 10 seconds to mix thoroughly (homogenize) and then left in the dark undisturbed (not agitated) until the product precipitates as nanofibers (FIG. 14).

Figure 15:
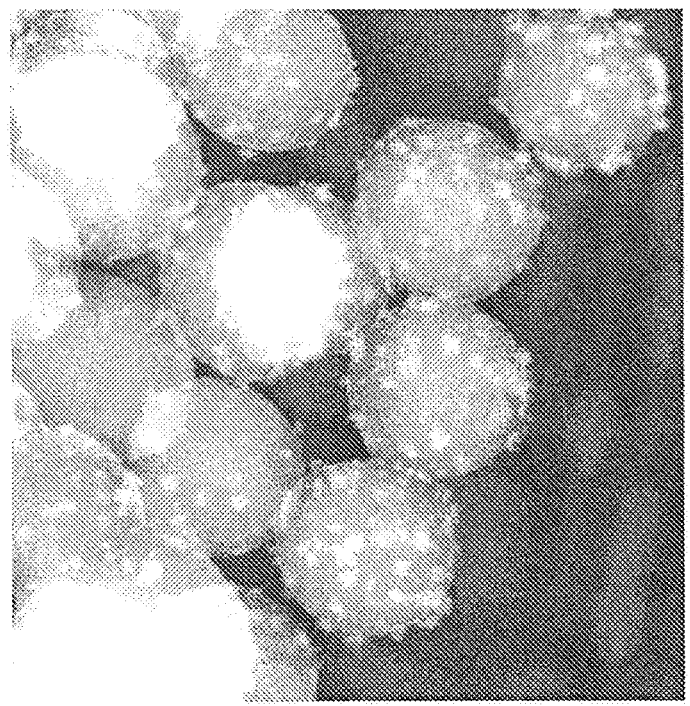
FIG. 15 is a dark-field scanning transmission electron micrograph (STEM) showing Pt nanodendrites grown photocatalytically on the surface of Pt—SnT4PyP nanospheres.

When the metalloporphyrin incorporated in the nanosphere has suitable excitation properties for use as a photocatalyst, metal can be photocatalytically deposited on the surface of the sphere. For the photo-metallization of the porphyrin spheres, the mixture of the colloidal suspension of nanospheres, a metal ion source, and an electron donor species should be stirred while being irradiated at a suitable wavelength. Examples of suitable electron donor species include but are not restricted to ascorbic acid, ethylenediamine tetraacetic acid and salts thereof, triethanolamine, methanol, and ethanol. Photochemical formation of metal dendrites on surfactant nanostructures has been described in J. A. Shelnutt, Y. Song, E. F. Pereira, and C. J. Medforth, "Dendritic Metal Nanostructures," filed Jul. 8, 2004, "U.S. patent application Ser. No. 10/887,535, which is incorporated herein by reference. Photochemical formation of metal dendrites on nanotubes has been described in J. A. Shelnutt, C. J. Medforth, and Z. Wang, "Heteroporphyrin Nanotubes and Composites," U.S. Pat. No. 7,132,163, which is incorporated herein by reference. FIG. 15 presents a dark-field scanning transmission electron microscopy image (STEM) of the Pt—SnT(4Py)P nanospheres coated with Pt dendrites. The nanospheres were platinized by 7 minutes of visible-light exposure in the presence of 10 mM ascorbic acid and 0.2 mM $K_2PtCl_4$. In this embodiment, 0.5 mL of a suspension of the Pt—SnT(4Py)P nanospheres in a 2-mL glass vial was combined with 0.5 mL of water, 50 μL of freshly prepared 0.2 M ascorbic acid, and 10 μL of aged 20 mM $K_2PtCl_4$ solution. The vial was placed in a glass water bath, and irradiated with incandescent light (800 nmol $cm^{-2}$ $s^{-1}$) from a projector lamp for 7 min.

Figure 16:
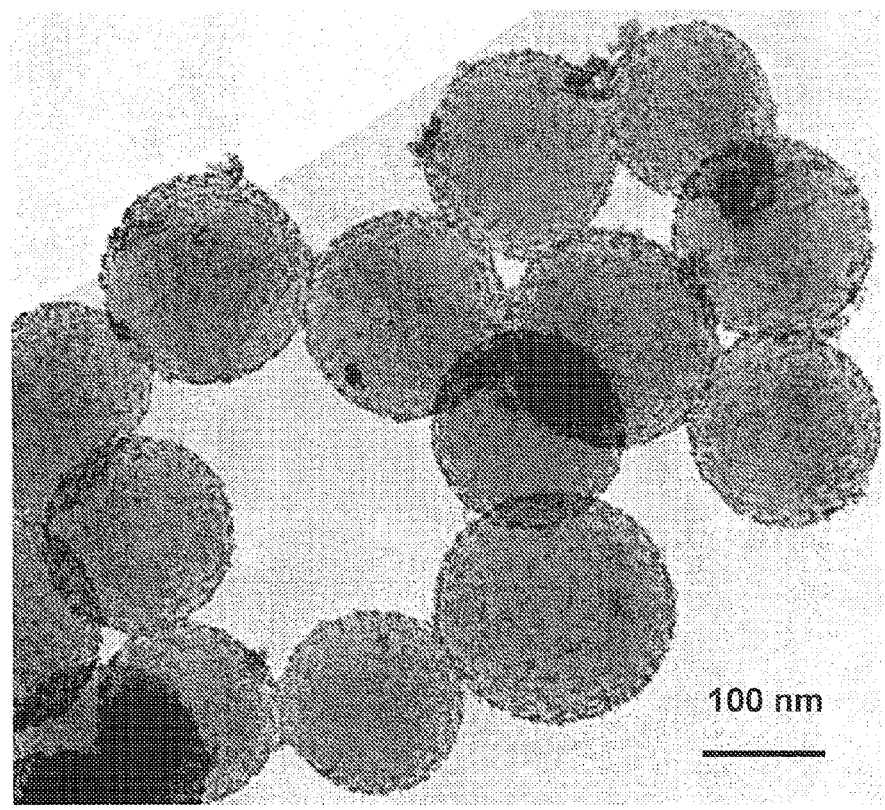
FIG. 16 is a TEM of a SnT (4Py)P nanosphere with Pt nanoparticles on the surface following chemical reduction by immersion in 0.1 M NaBH$_4$ for 3 h.

Chemical reduction may also be employed in some embodiments. In one embodiment, 1 mg of the Pt—SnT(4-Py)P nanospheres was immersed in 10 mL of 0.1 M $NaBH_4$ for 3 hours. The product was recovered by three cycles of centrifugation and re-dispersion in water. The chemically reduced nanospheres are illustrated in the TEM image of FIG. 16, which shows nanocomposite spheres with dense and highly uniform coverage of Pt nanoparticles on the surface. The Pt particles are highly branched and irregular in shape, and extend from 3 to 10 nm.

In one embodiment, 1 mg of the Pt—SnT(4-Py)P nanospheres was immersed in 10 mL of 0.1 M $N_2H_4$ for 3 hours. The product was recovered by three cycles of centrifugation and re-dispersion in water.

The foregoing description of the invention has been presented for purposes of illustration and description and is not intended to be exhaustive or to limit the invention to the precise form disclosed, and obviously many modifications and variations are possible in light of the above teaching. The embodiments were chosen and described in order to best explain the principles of the invention and its practical application to thereby enable others skilled in the art to best utilize the invention in various embodiments and with various modifications as are suited to the particular use contemplated. It is intended that the scope of the invention be defined by the claims appended hereto.

What is claimed is:

1. A method for fabricating a porphyrin coordination polymer nanostructure, the method comprising:
   combining an aqueous solution of a pyridylporphyrin and an aqueous solution of connecting metal ions to form an aqueous reaction solution, the pyridylporphyrin comprising at least two pyridyl groups; and
   forming the porphyrin coordination polymer nanostructure in the aqueous reaction solution by reactively forming coordinate bonds between a plurality of pyridyl groups of the pyridylporphyrin and a plurality of the connecting metal ions, wherein agitation during the step of forming the porphyrin coordination polymer nanostructure is sufficiently minimized to provide a majority of substantially spherical nanostructures and a minority of rod-like nanostructures.

2. The method of claim 1, wherein the step of forming the porphyrin coordination polymer nanostructure is performed substantially in the dark.

3. The method of claim 1, further comprising agitating the reaction solution during at least part of the step of forming the porphyrin coordination polymer nanostructure.

4. The method of claim 1, wherein the pyridylporphyrin is selected from the group consisting of meso-tetra(4-pyridyl)porphyrin, meso-tetra(3 pyridyl)porphyrin, and mesodiphenyldipyridylporphyrin.

5. The method of claim 1, wherein the pyridylporphyrin is a metalloporphyrin.

6. The method of claim 5, wherein the pyridylporphyrin is a metalloporphyrin wherein a metal of the metalloporphyrin is selected from the group consisting of Sn, Fe, Co, Cu, TiO, and VO.

7. The method of claim 1, further comprising:
isolating the porphyrin coordination polymer nanostructure from the aqueous reaction solution;
combining the porphyrin coordination polymer nanostructure, metal ions from a metal salt, and an electron donor species in an aqueous suspension; and
reducing the metal ions to form dendritic metal nanostructures on the porphyrin coordination polymer nanostructure.

8. The method of claim 7, wherein the pyridylporphyrin is a metalloporphyrin and further comprising irradiating the aqueous suspension with light of a wavelength that causes electronic excitation of the metalloporphyrin to form a reduced photocatalyst, and wherein the metal ions have reduction potentials for reduction to a zero-valent state such that reduction of the metal ions by the reduced photocatalyst produces a dendritic metal nanostructure on the porphyrin coordination polymer nanostructures.

9. The method of claim 7, wherein the electron donor species is selected from the group consisting of ascorbic acid, ethylenediamine tetraacetic acid and salts thereof, triethanolamine, methanol, and ethanol.

10. The method of claim 7, wherein the metal salt comprises a salt selected from a group consisting of salts of Pt, Pd, Au, Ag, Ir, Ru, and Rh.

11. The method of claim 1, further comprising:
reducing a portion of the connecting metal ions to form metal nanoparticles on the porphyrin coordination polymer nanostructure.

* * * * *